(12) United States Patent
Schwartzer et al.

(10) Patent No.: US 10,408,748 B2
(45) Date of Patent: Sep. 10, 2019

(54) SYSTEM AND METHOD FOR EVALUATING FRUITS AND VEGETABLES

(71) Applicant: ClariFruit, Rishon LeZion (IL)

(72) Inventors: Avi Schwartzer, Irus (IL); Ruby Boyarksi, Ness Ziona (IL)

(73) Assignee: ClariFruit, Rishon LeZion (IL)

( * ) Notice: Subject to any disclaimer, the term of this patent is extended or adjusted under 35 U.S.C. 154(b) by 0 days.

(21) Appl. No.: 15/878,429

(22) Filed: Jan. 24, 2018

(65) Prior Publication Data

US 2018/0209901 A1   Jul. 26, 2018

Related U.S. Application Data

(60) Provisional application No. 62/450,601, filed on Jan. 26, 2017.

(51) Int. Cl.
| | |
|---|---|
| *G01N 21/35* | (2014.01) |
| *G01N 21/3563* | (2014.01) |
| *G01N 21/359* | (2014.01) |
| *G01N 33/02* | (2006.01) |
| *G01N 21/84* | (2006.01) |

(52) U.S. Cl.
CPC ....... *G01N 21/3563* (2013.01); *G01N 21/359* (2013.01); *G01N 33/025* (2013.01); *G01N 2021/8466* (2013.01); *G01N 2201/0221* (2013.01); *G01N 2201/12* (2013.01)

(58) Field of Classification Search
CPC . G01N 21/3563; G01N 21/359; G01N 33/025
See application file for complete search history.

(56) References Cited

U.S. PATENT DOCUMENTS

| | | | | | |
|---|---|---|---|---|---|
| 5,729,473 | A | * | 3/1998 | Blanc | B07C 5/342 209/580 |
| 7,319,990 | B1 | * | 1/2008 | Henty | G01G 19/4144 356/326 |
| 2002/0011567 | A1 | * | 1/2002 | Ozanich | G01J 3/02 250/326 |
| 2010/0297291 | A1 | * | 11/2010 | Shinoda | G01N 21/359 426/15 |
| 2011/0261355 | A1 | * | 10/2011 | Hannel | G01J 3/0291 356/303 |

* cited by examiner

*Primary Examiner* — Hugh Maupin
(74) *Attorney, Agent, or Firm* — Vorys, Sater, Seymour and Pease LLP

(57) ABSTRACT

A system and method for non-destructively determining characteristics of a vegetable or fruit may include processing an image of the vegetable or fruit to produce image analysis results; analyzing light emitted by a Near Infrared Reflectance (NIR) device and reflected from the vegetable or fruit to produce reflection analysis results; and calculating at least one value that reflects at least one characteristic of the vegetable or fruit based on the image analysis results and based on the reflection analysis results.

20 Claims, 8 Drawing Sheets

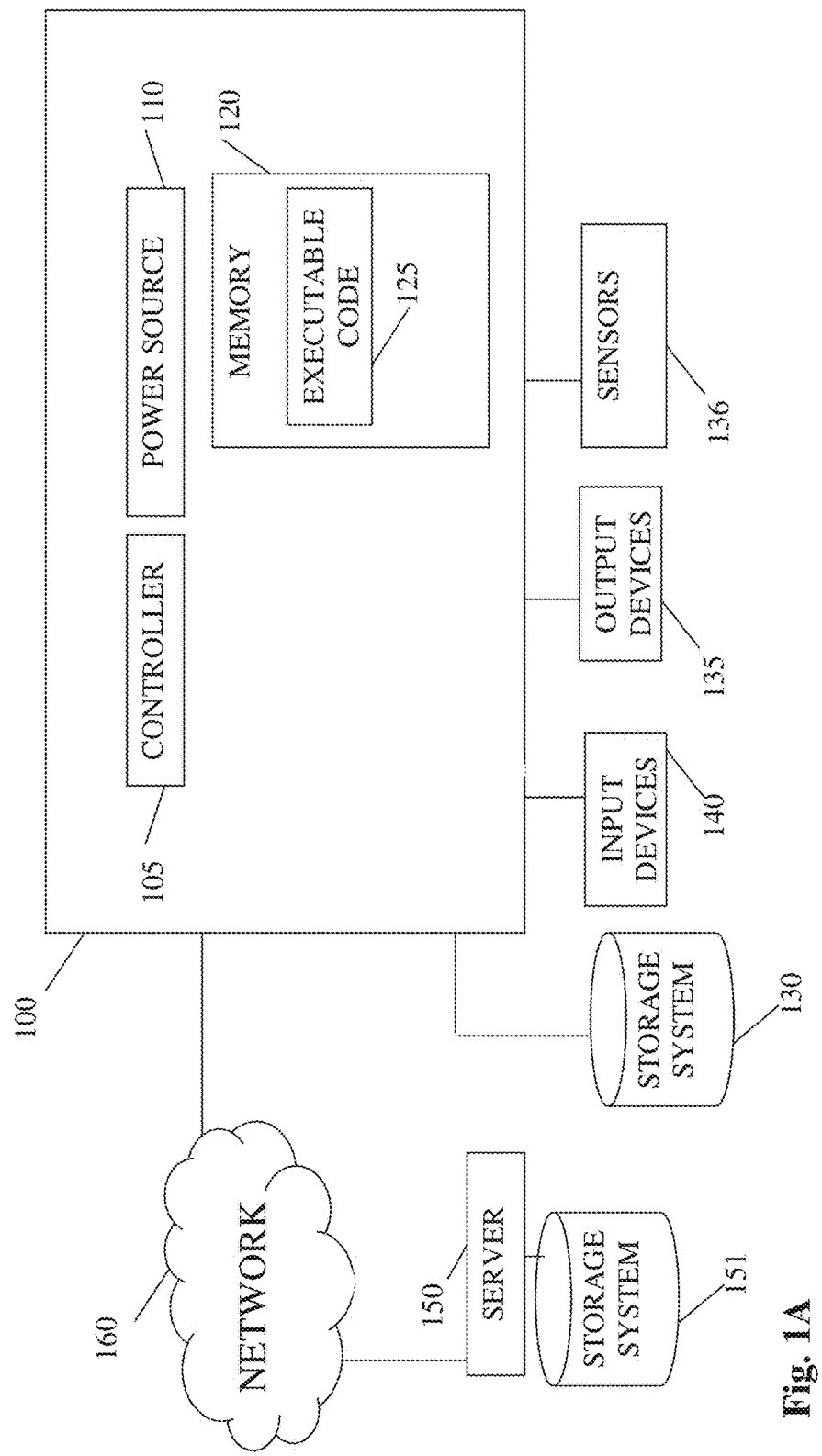

| Type | Fruit Mater (BRIX) | Polarity (BRIX) | Diff (%) |
|---|---|---|---|
| Scarlotta | 17.1% | 16.5% | 13% |
| Zani | 17.6% | 16.9% | 14% |
| Autumn Crisp | 17.2% | 16.4% | 10% |

| Type | Fruit Meter (mm) | Polarity (g) | Relation Diff (%) |
|---|---|---|---|
| Scarlotta | 22 | 8.2 | 12% |
| Zani | 20 | 8.1 | 14% |
| Autumn Crisp | 24 | 8.5 | 15% |

SYSTEM AND METHOD FOR EVALUATING FRUITS AND VEGETABLES

CROSS-REFERENCE TO RELATED APPLICATIONS

This application claims the benefit of U.S. Provisional Patent Application No. 62/450,601, entitled "SYSTEM AND METHOD FOR EVALUATING SUBSTANCE", filed on Jan. 26, 2017, which is incorporated herein by reference in its entirety.

FIELD OF THE INVENTION

The present invention relates generally to evaluating substance. More specifically, the present invention relates to using a computing device and sensors to determine attributes and characteristics of a vegetables or fruits.

BACKGROUND OF THE INVENTION

The need to evaluate fruits and vegetables is known in the art. For example, the ripeness of a fruit is of crucial importance to a buyer and/or grower of the fruit, the sugar level is of crucial importance when using vegetables to feed livestock and so on. There currently exists no system or method for readily and quickly, using a small, portable computing device, for evaluating attributes of a fruits or vegetables. For example, by merely looking at a fruit (e.g., a watermelon or avocado), it may be impossible to determine ripeness, sugar level and the like or determine how long the fruit has been shelved.

SUMMARY OF THE INVENTION

An embodiment for non-destructively determining characteristics of a vegetable or fruit may include processing an image of vegetable or fruit to produce image analysis results; analyzing light emitted by a Near Infrared Reflectance (NIR) device and reflected from the vegetable or fruit to produce reflection analysis results; and calculating at least one value that reflects at least one characteristic of the vegetable or fruit based on the image analysis results and based on the reflection analysis results.

An embodiment may include calculating a first value that represents a ripeness and a second value that represents a quality; and presenting the values to a user. An embodiment may include obtaining a cultivar of the vegetable or fruit; and calculating the at least one value based on the cultivar. Calculating the at least one value may be based on at least one of: a geographic region, a temperature and a date. Calculating the at least one value may be for a plurality of vegetables or fruits.

An embodiment may calculate a prediction related to at least one of: harvesting and treating of crops. An embodiment may create a profile and may associate the profile with a score; and the embodiment may calculate at least one value based on the profile and score. An embodiment may use input from a plurality of sources for at least one of: creating the profile and calculating the score.

An embodiment may designate at least one of: a profile and a score, as a reference; and may calculate at least one value based on comparing at least one reference to at least one of: the image analysis results and the reflection analysis results. An embodiment may cause a machine to select a fruit or vegetable based on at least one of: a profile and a score. Other aspects and/or advantages of the present invention are described herein.

BRIEF DESCRIPTION OF THE DRAWINGS

Non-limiting examples of embodiments of the disclosure are described below with reference to figures attached hereto that are listed following this paragraph. Identical features that appear in more than one figure are generally labeled with a same label in all the figures in which they appear. A label labeling an icon representing a given feature of an embodiment of the disclosure in a figure may be used to reference the same given feature in other embodiments. Dimensions of features shown in the figures are chosen for convenience and clarity of presentation and are not necessarily shown to scale.

The invention, features and advantages thereof, may best be understood by reference to the following detailed description when read with the accompanied drawings. Embodiments of the invention are illustrated by way of example and not limitation in the figures of the accompanying drawings, in which like reference numerals indicate corresponding, analogous or similar elements, and in which:

FIG. 1A shows high level block diagram of a system according to illustrative embodiments of the present invention;

Figure 1B:
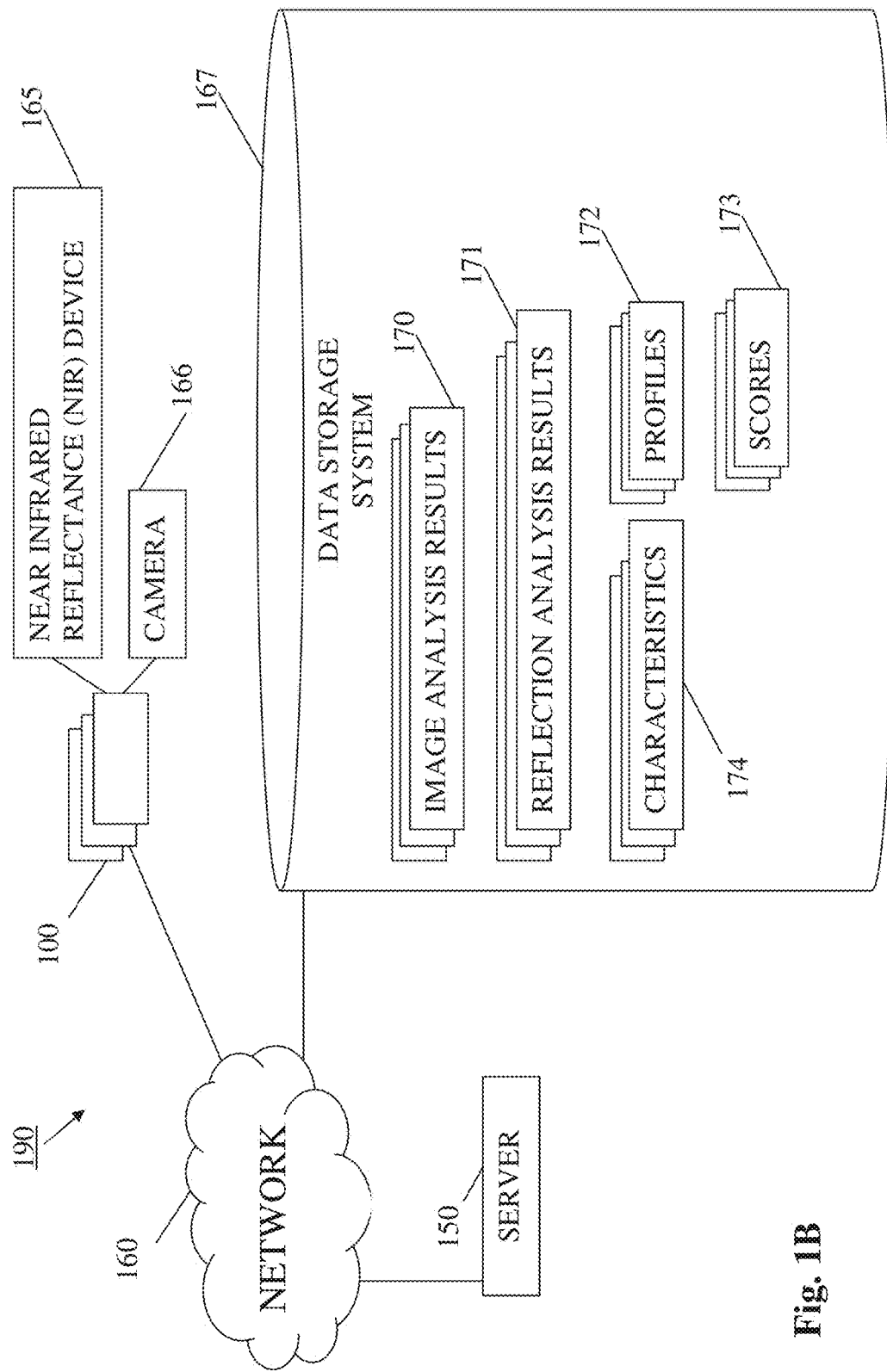
FIG. 1B shows high level block diagram of a system according to illustrative embodiments of the present invention.

It will be appreciated that, for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although some embodiments of the invention are not limited in this regard, discussions utilizing terms such as, for example, "processing," "computing." "calculating," "determining," "establishing". "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Reference is made to FIG. 1A, showing a high-level block diagram of an exemplary computing device 100 according to some embodiments of the present invention. Computing device 100 may be, or components of computing device 100 may be included in, a mobile computing device, e.g., a laptop, tablet, cell phone or smartphone as known in the art.

Computing device 100 may include a controller 105 that may be, for example, a central processing unit processor (CPU), a chip or any suitable computing or computational device, an operating system 115, a memory 120, executable code 125, a storage system 130, input devices 135, sensors 136 and output devices 140. Controller 105 (or one or more controllers or processors, possibly across multiple units or devices) may be configured to carry out methods described herein, and/or to execute or act as the various modules, units, etc. More than one computing device 100 may be included in, and one or more computing devices 100 may be, or act as the components of, a system according to some embodiments of the invention.

More than one computing device 100 may be included, and one or more computing devices 100 may act as the various components, for example the components of system a system as described herein. For example, a plurality of computing devices 100 may be used by a plurality of users and scores or preferences of provided by the plurality of users may be received. e.g., by server 150 and used for generating a universal or global measurable fruit quality meter, reference or measure. For example, a universal or global quality meter value or score, adopted by farmers, wholesalers, resellers, retailers and consumers, may be used to improve or standardize quality or other aspects related to the fresh food supply chain, from the farmer fields all the way to the consumers.

Operating system 115 may be or may include any code segment (e.g., one similar to executable code 125 described herein) designed and/or configured to perform tasks involving coordination, scheduling, arbitration, supervising, controlling or otherwise managing operation of computing device 100, for example, scheduling execution of software programs or enabling software programs or other modules or units to communicate. Operating system 115 may be a commercial operating system, e.g., Android, iOS and the like. e.g., in embodiments where computing device 100 is a mobile computing device, e.g., a laptop, tablet, cell phone or smartphone.

Memory 120 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short-term memory unit, a long-term memory unit, or other suitable memory units or storage units. Memory 120 may be or may include a plurality of, possibly different memory units. Memory 120 may be a computer or processor non-transitory readable medium, or a computer non-transitory storage medium, e.g., a RAM.

Executable code 125 may be any executable code, e.g., an application, a program, a process, task or script. Executable code 125 may be executed by controller 105 possibly under control of operating system 115. For example, executable code 125 may be an application that, using input from sensors 136 and data received from server 150 or other sources, evaluates, calculates and/or determines attributes, characteristics, classification, description and/or other aspects related to a substance such as a fruit or vegetable as further described herein.

Although, for the sake of clarity, a single item of executable code 125 is shown in FIG. 1A, a system according to some embodiments of the invention may include a plurality of executable code segments similar to executable code 125 that may be loaded into memory 120 and cause controller 105 to carry out methods described herein.

Storage system 130 may be or may include, for example, a hard disk drive, a flash memory, a universal serial bus (USB) device or other suitable removable and/or fixed storage unit. Content may be stored in storage system 130 and may he loaded from storage system 130 into memory 120 where it may be processed by controller 105. In some embodiments, some of the components shown in FIG. 1A may be omitted. For example, memory 120 may be a non-volatile memory having the storage capacity of storage system 130. Accordingly, although shown as a separate component, storage system 130 may be embedded or included in memory 120.

Input devices 135 may be or may include a mouse, a keyboard, a touch screen or pad or any suitable input device. It will be recognized that any suitable number of input devices may be operatively connected to computing device 100 as shown by block 135. Output devices 140 may include one or more displays or monitors, speakers and/or any other suitable output devices. It will be recognized that any suitable number of output devices may be operatively connected to computing device 100 as shown by block 140. Any applicable input/output (I/O) devices may be connected to computing device 100 as shown by blocks 135 and 140. For example, a wired or wireless network interface card (NIC), a printer, a universal serial bus (USB) device or external hard drive may be included in input devices 135 and/or output devices 140.

A system according to some embodiments of the invention may include components such as, but not limited to, a plurality of central processing units (CPU) or any other suitable multi-purpose or specific processors or controllers (e.g., controllers similar to controller 105), a plurality of input units, a plurality of output units, a plurality of memory units, and a plurality of storage units. A system may additionally include other suitable hardware components and/or software components. In some embodiments, a system may include or may be, for example, a personal computer, a desktop computer, a laptop computer, a workstation, a server computer, a network device, or any other suitable computing device. For example, a system as described herein may include one or more devices such as computing device 100.

Sensors 136 may be any suitable sensors. In some embodiments, sensors 136 may be any sensors that can monitor, detect or determine external and internal attributes of vegetables, fruit and/or other food. For example, using techniques involving light reflection, sound reflection and image processing, sensors 136 may obtain information related to a substance in a none destructive way (e.g., without damaging, or otherwise causing any change to a fruit or vegetable being evaluated).

Network 160 may be, may comprise or may be part of a private or public IP network, or the internet, or a combination thereof. Additionally, or alternatively, network 160 may be, comprise or be part of a global system for mobile communications (GSM) network. For example, network 160 may include or comprise an IP network such as the internet, a GSM related network and any equipment for bridging or otherwise connecting such networks as known in the art. In addition, network 160 may be, may comprise or be part of an integrated services digital network (ISDN), a public switched telephone network (PSTN), a public or private data network, a local area network (LAN), a metropolitan area network (MAN), a wide area network (WAN), a wireline or wireless network, a local, regional, or global communication network, a satellite communication network, a cellular communication network, any combination of the preceding and/or any other suitable communication means. Accordingly, numerous elements of network 160 are implied but not shown, e.g., access points, base stations, communication satellites, GPS satellites, routers, telephone switches, etc. It will be recognized that embodiments of the invention are not limited by the nature of network 160. Server 150 may be a server as known in the art, e.g., a web or another server that may include components of computing device 100, e.g., a controller 105, memory 120 and executable code 125. Storage system 151 may be operatively connected to server 150 as shown, storage system 151 may be any suitable storage system, e.g., a database as known in the art.

Reference is made to FIG. 1B, showing a high-level block diagram of a system 190 according to some embodiments of the present invention. As shown, a system may include a plurality of computing systems or devices 100 (e.g., a plurality of users' smartphones or other mobile communication devices), a server 150 and a digital data storage system 167 that may be, or may be similar to, storage systems 130 and/or 151. As shown, some of computing devices 100 may include, or may be connected to, a camera 166 and NIR device 165. Camera 166 may be any suitable image acquisition device capable of obtaining an image of an object, for example, in some embodiments, camera 166 is included in a smartphone as known in the art. NIR 165 may be a device that emits infrared light onto an object (e.g., a fruit or vegetable) and receives or senses (e.g., using a built-in sensor) infrared light reflected from the object.

As shown, data storage system 167 may store or include image analysis results 170, reflection analysis results 171, profiles 172, scores 173 and characteristics 174. Profiles 172 may be, or may include any information in, profile 220 described herein and scores 173 may be, or may include any information in, scores 221 described herein. Image analysis results 170, reflection analysis results 171, profiles 172, scores 173 and characteristics 174 may be, or may include, any suitable digital data structure or construct or computer data objects that enable storing, retrieving and modifying digital data, values or information. For example, some of image analysis results 170, reflection analysis results 171, profiles 172, scores 173 and characteristics 174 may be or may include files, tables or lists in a database in storage system 167. For example, some of image analysis results 170, reflection analysis results 171, profiles 172, scores 173 and characteristics 174 may each include several fields that can be digitally set or cleared by controller 105, a plurality of parameters for which values can be set by controller 105, a plurality of entries that may be modified by controller 105 or by server 150 and so on. For the sake of simplicity, image analysis results 170, reflection analysis results 171, profiles 172, scores 173 and characteristics 174 may be collectively referred to herein, e.g., by image analysis results 170 or individually, e.g., by image analysis result 170.

Figure 2:
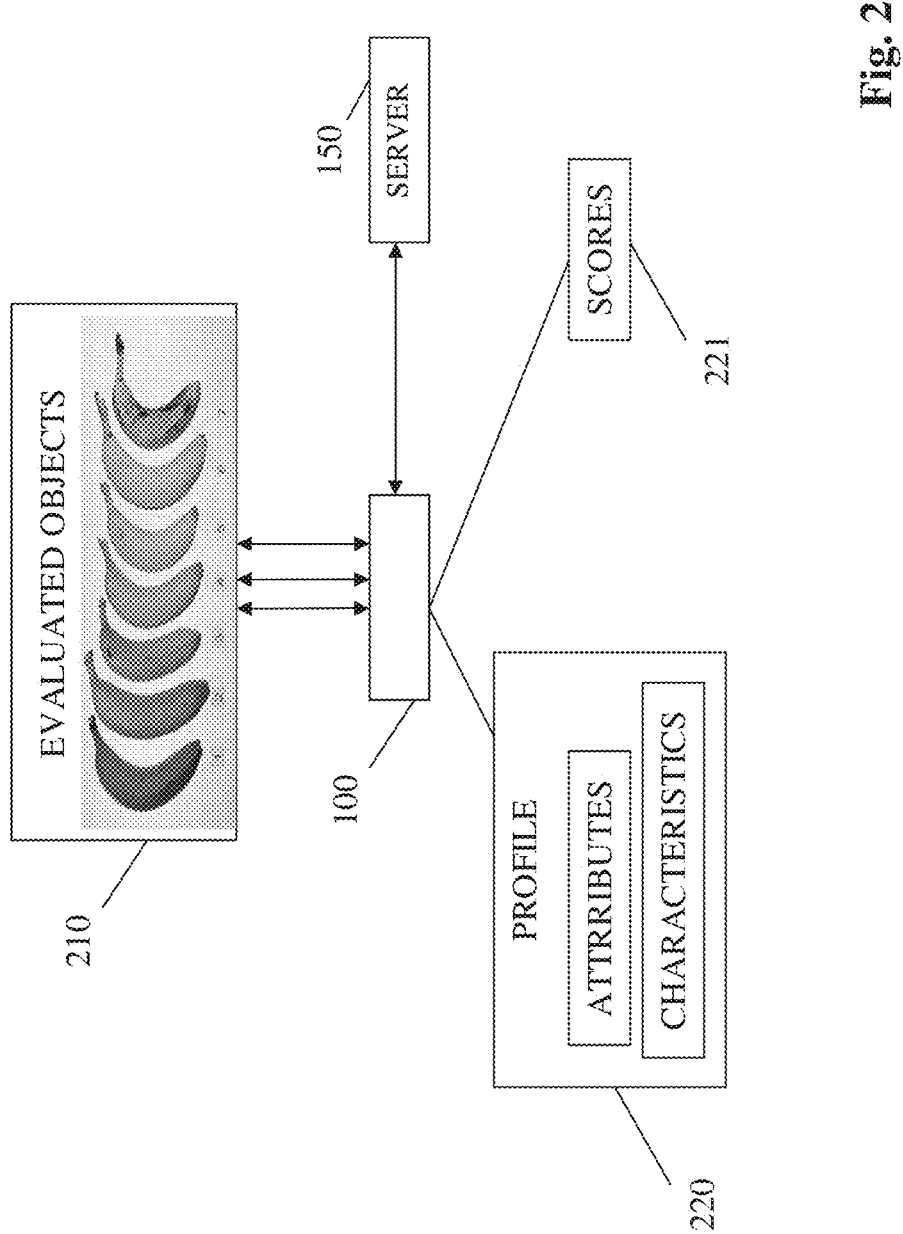
FIG. 2 is an overview of a flow according to illustrative embodiments of the present invention.

Reference is made to FIG. 2, which shows an overview of a system 200 and flows according to some embodiments of the present invention. As shown, evaluated objects 210 may be examined and profiled by computing device 100 and create or determine profile 220. As shown, profile 230 may include any attributes, and/or characteristics of one or more of evaluated objects 210.

For example, using input from sensors 136 and/or I/O devices 135 and 145, profile 220 of an evaluated object 210, e.g., an orange, that includes the size, color, weight, sugar level and acidity level of evaluated object (or profiles of objects) 210 may be determined, identified or calculated and provided as shown by blocks 220. Using input from sensors 136 and/or I/O devices 135 and 145, level, a profile 220 that includes the percentage, concentration or amount of water, fat, sugar or other substances, in evaluated object 210, may be determined, identified or calculated. Any other aspects of evaluated object 210, e.g., firmness, texture or smell may be determined, identified, calculated and included in its profile, for example, using input from sensors 136 and/or I/O devices 135 and 145 and input from server 150 as shown.

Any system or method known in the art may be used for generating or creating a profile 220 that includes attributes and characteristics or any relevant description. For example, image processing of an image of evaluated objects 210, light reflection or penetration or any other methods may be used to determine a description that includes color, substance levels, amounts or concentrations (e.g., sugar level, acidity and the like). Accordingly, a user may point his or her smartphone at a fruit and be provided with a profile 220 of the fruit.

Figure 5:
FIG. 5 is shows screenshots according to illustrative embodiments of the present invention.

Reference is additionally made to FIG. 5, which shows screenshots according to some embodiments of the invention. As shown, e.g., following pointing a smartphone (or a unit attached to the smartphone) at a fruit, characteristics, scores, amounts, concentrations or measures of color, acidity, water, BRIX, size and sugar may be presented to a user. A score or measure of ripeness or freshness may be displayed or presented as further shown. It will be understood that FIG. 5 shows an example of a presentation of information and that any other characteristics, attributes, scores, profiles or descriptions related to an evaluated object may be presented.

A profile may be scored. For example, different profiles of a banana may be differently scored. For example, a set of specific scores, for a respective set of profiles of a fruit may be calculated or obtained, stored, e.g., by server 150 and may be used as described. As described, each profile (e.g., of a banana or orange) describes or includes a set of values that describes or characterizes an object, e.g., a profile may describe an orange with a specific sugar level and so on as described.

For example, two different scores may be associated, e.g., by server 150 and/or by computing device 100, with two respective, profiles of bananas, e.g., a score of 6 may be associated with a profile of a yellow banana and a score of 4.8 may be associated with a profile of a grinner banana, the two bananas may otherwise be same or identical, e.g., picked from the same tree on the same day.

A score may be calculated by computing device 100 by determining or calculating a profile of an object and matching the profile with a score as provided, e.g., by server 150 as described.

For example, after determining, based on an image of evaluated objects 210 that evaluated objects 210 are bananas (e.g., using object recognition as known in the art), computing device 100 may request, from server 150, a scoring table (or any other data object or construct) for a banana. A scoring table for a banana may include a set of scores for a respective set of profiles of bananas. For example, a profile of a banana with a first set of size, color and sugar level may be associated with (or given) a first score, a profile of a banana with a second set of size, color and sugar level may be associated with (or given) a second score and so on.

Accordingly, some of the scores 221, attributes and characteristics in profile 220 determined for an evaluated substance may be based on quantities or attributes measured or determined by computing device 100 (e.g., based on a color, size, light absorption and the like) and some of the profile, scores, attributes and characteristics determined for an evaluated object may be based on information received from server 150. As further described herein, information stored in, and provided by server 150 may include information received from a community of users. For example, based on information from a community of users, a banana with a specific profile (e.g., specific color, size or sugar level) may be given a high score.

Block 230 shows exemplary attributes and characteristics that may be determined, identified or calculated for an evaluated substance 220. As shown, average values of sugar level, acidity, pH, ripeness, flavor and the like may be measured, determined or deduced based on input from sensors 136 and input from server 150 as described.

Figure 3:
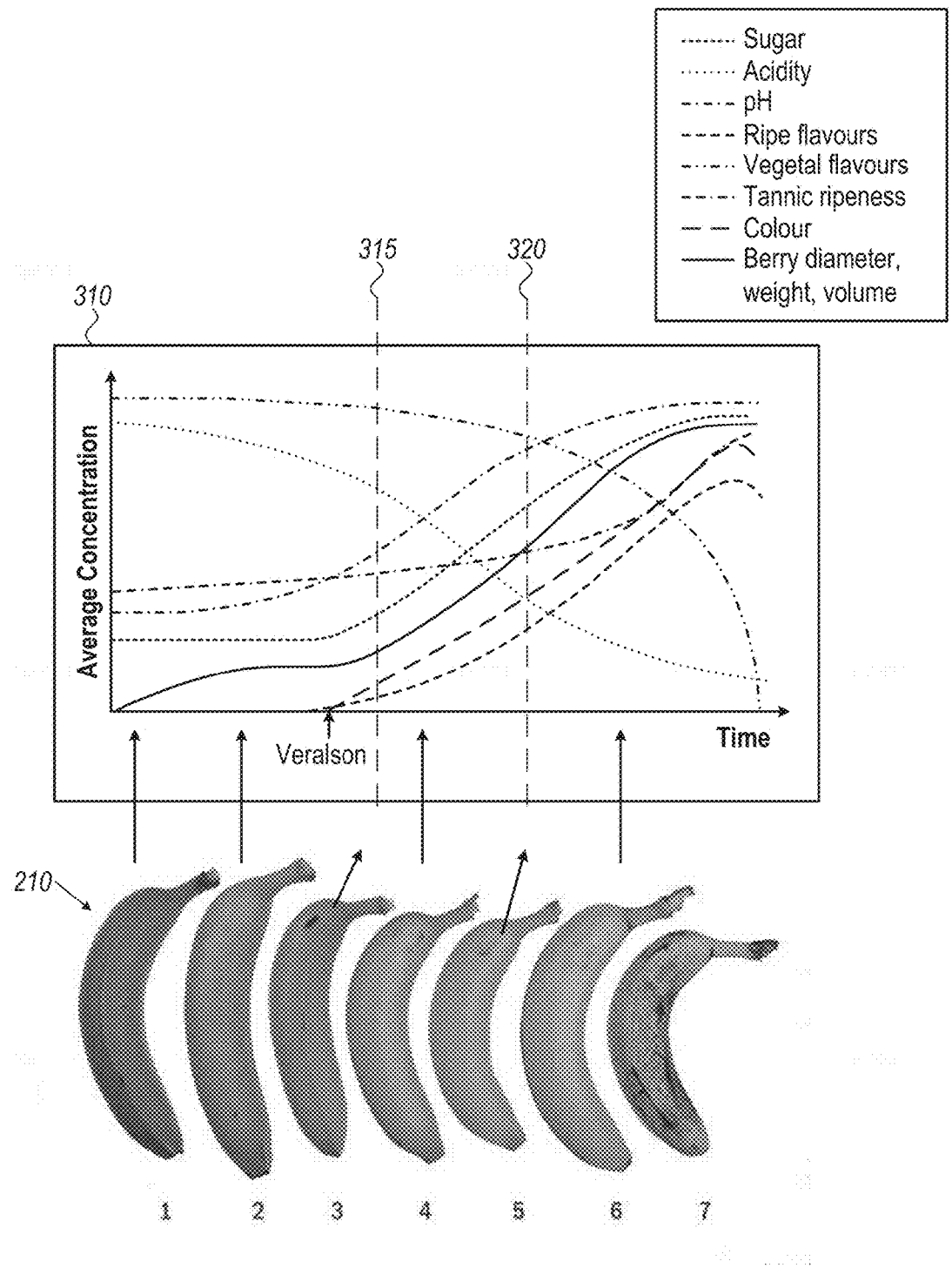
FIG. 3 shows attributes over time of evaluated substance according to illustrative embodiments of the present invention.

Reference is made to FIG. 3, which shows, in block 310, the evolution of attributes of an evaluated object, over time, according to illustrative embodiments of the present invention. As shown, attributes and characteristics that may be determined, identified or calculated for an evaluated object 210 may include values, concentrations, amounts or other quantities such as sugar level, acidity, pH, ripeness, flavor and the like.

Vertical lines 315 and 320 graphically show, indicate or represent profiles. As shown by vertical lines 315 and 320, a profile that includes a specific set of attributes or characteristics may be defined and stored. For example, a profile with a first set of attributes or characteristics may be defined by the intersection of line 315 with each of the concentrations or values of sugar, acidity etc. such that the set (or specific values) of attributes or characteristics in a profile specifically and uniquely describe a specific vegetable or fruit. A second profile with, or including, a second set of attributes or characteristics may be defined by the intersection of line 320 with each of the concentrations or values of sugar, acidity etc.

For example, profile 315 may represent banana 3 and profile 320 may represent banana 5 as shown. Similarly, although not shown, profiles for bananas 1, 2, 4 and 6-7 may be defined. For example, using profiles as described, a user may precisely select a banana, e.g., the difference between bananas 5 and 6 in FIG. 3 may be difficult (or even impossible) for a human to identify or determine, but, using an embodiment of the invention as described, a user may easily and readily distinguish between bananas 5 and 6 in FIG. 3. For example, a recipe for a banana bread may include profile 315, thus enabling a user to select a banana that is the same (e.g., with respect to ripeness, sugar level etc.) as the one used by a chef who provided the recipe.

Scores may be assigned to, or associated with profiles. For example, and as shown, the sugar level or concentration defined by profile or line 315 is lower than that of profile or line 320, but the weight is higher; thus, if weight is preferred, profile or line 315 may be scored higher than profile or line 320, but if sweetness or taste are of the greatest importance, then profile or line 320 may be scored higher than profile or line 315. Any system, method or logic may be used to score profiles as described.

The information graphically shown in FIG. 3 may be stored in server 150 and/or in computing device 100. For example, a set of scores for a respective set of profiles may be stored in server 150 and/or in computing device 100 and accordingly, based on attributes or characteristics of an evaluated object, or based on a match of a profile of an evaluated object with a known profile, a score may be determined and/or produced.

Accordingly, a universal measurable fruit quality meter may be provided by some embodiments. A universal measurable fruit quality meter may be used to improve the efficiency of the fresh food supply chain, from the farmer fields all the way down to the consumers, for example, the farmer, retailer and consumer may all use the same set of attributes or characteristics to score, mark or price vegetables and fruits.

Figure 4:
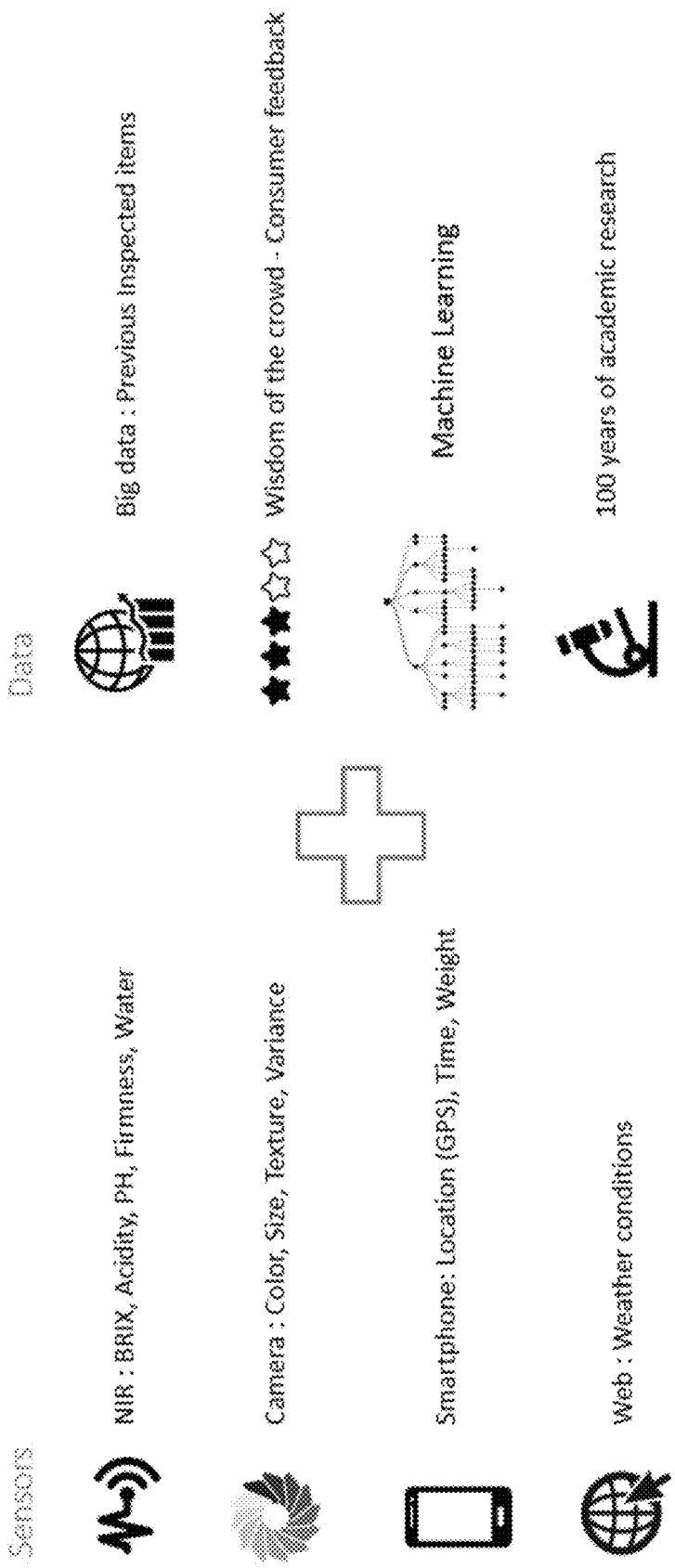
FIG. 4 is an overview of data used according to illustrative embodiments of the present invention.

Reference is made to FIG. 4, which shows an overview of data used for evaluating or characterizing fruits and vegetables according to illustrative embodiments of the present invention. It will be noted that, although some known systems and methods may include measuring attributes of vegetables, none of the known systems and methods include augmenting data from sensors and from a set of sources as shown by FIG. 4. For example, by using data recorded, measured or obtained by sensors of, or connected to a smartphone or other computing device and data from labs, previously analyzed fruits, academic research, whether, locale and other sources as shown by FIG. 4, embodiments of the invention provide unprecedented results, e.g., precise characteristics and predictions as described herein.

As shown, sensors, e.g., in, or connected to, a computing device 100 may obtain various attributes or characteristics of an evaluated substance, e.g., fruit or vegetable, e.g., attributes or characteristics such as BRIX, acidity, pH level, firmness and water amount or concentration, color, size, texture and the like may be obtained. Color, size, weight and the like may also be determined, e.g., using a camera of a smartphone, an image of a vegetable may be acquired and using image processing as known in the art, the colors (or a histogram of colors) and size may be determined. Input from any sensors may be used, e.g., weight, smell and the like may be obtained and used to characterize, score or describe substance as described. Any data that may be relevant may be used. For example, since crop quality or characteristics may depend on location and/or weather conditions, information related to weather conditions and locale (e.g., the weather in the era where a specific fruit was grown) may be used as input to an evaluation process.

Data such as recorded scores or attributes of fruits and vegetables (e.g., as measured in labs), feedback from users and academic researches may all be used. For example, lab results e.g., recording, for various substances such as fruits and vegetables, images, color, size, substance concentrations and the like, comparing the results to known results, calculating or determining various attributes such as ripeness, juiciness, getting input from users (e.g., scores for different sets of characteristics and storing and data for further processing.

A community of users may score objects and a global or other score may be calculated or determined based on users' scores (e.g., as shown by consumer feedback and/or wisdom of the crowd in FIG. 4). For example, the most popular (among a community of users) profile of a banana may be published by server 150, a user may download the profile to his or her smartphone, point the smartphone at a set of bananas and the smartphone may draw a circle, on the smartphone's screen, around the image of a banana in the set that has the same profile as the downloaded profile. A recipe, or a chef in a TV show, may provide the profiles of the fruits or vegetables he or she uses such that users may better use cooking or baking recipes. Pricing of fruit and vegetables may be based on profiles or scores etc. Automated machines in packaging facilities may select fruits and vegetables based on profiles and/or scores.

Weather and location data may be used, by an embodiment, to provide predictions or suggestions, e.g., when to harvest a crop, when a crop's quality is expected to be the highest, detect an abnormally during growth (e.g., a sugar level is too high or low) and so on. For example, an orange in a citrus grove may be evaluated by an embodiment as described (e.g., using an image and light reflection as described), and a prediction may be generated based on measured aspects and research or lab data. For example, based on sugar level, ripeness level and the like, and based on expected weather conditions, an embodiment may predict that the oranges in the citrus grove will be ready for picking in two weeks and that in five weeks the oranges will be too ripe, etc.

As shown by FIG. 4, any information may be used to evaluate substance such as fruit or vegetables. For example, big data that may include attributes, scores or other data or information related to fruit and vegetables may be used. Big data may be or may include data stored in databases, e.g., data in internet sites, academic institutions, research labs and the like. Machine learning may be used, e.g., based on results or evaluation of a set of vegetables or based on input from users that indicates accuracy or other aspects, an application on a smartphone or in a server may modify coefficients, weights, factors or other parameters used by logic that generates a score for an evaluated vegetable.

An embodiment may identify a fruit or vegetable (e.g., whether it is a climacteric or non-climacteric fruit and, based on the identification, select a logic for evaluation, provide output and suggestions and so on. For example, for a climacteric fruit, an embodiment may determine a ripeness level and the embodiment may determine the freshness level for a non-climacteric fruit.

A score may be calculated for a set or group of vegetables or fruit. For example, an embodiment may receive an image of a box of fruits, identify and evaluate some or even all of the fruits and provide a score for the group, e.g., an average score, the scores of the best and worst fruits in the box, expected time when fruit will no longer be good enough for selling or eating and so on.

Figure 6:
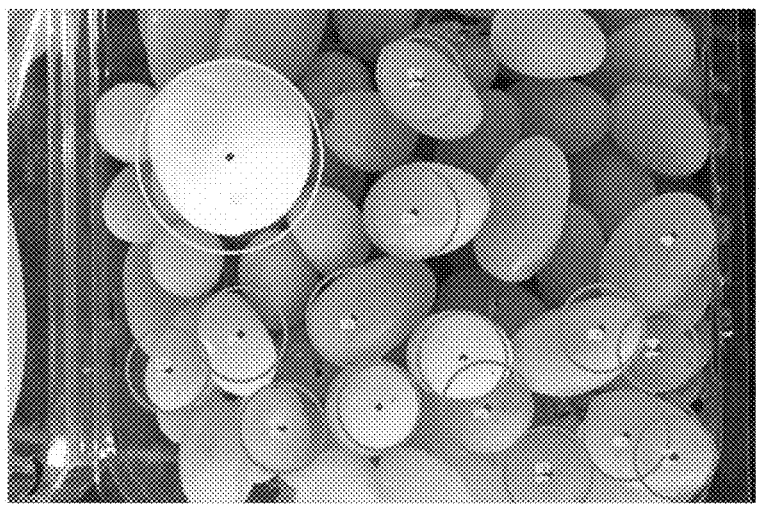
FIG. 6 is shows screenshots according to illustrative embodiments of the present invention.

Reference is made to FIG. 6, which illustrates identifying fruit (grapes) and example results or scores. As shown in FIG. 6, an embodiment may identify any number of fruits in a box, evaluate the fruits and generate scores for the fruits. As shown, various attributes of the fruits may be calculated, determined, presented and/or used as described herein.

Figure 7:
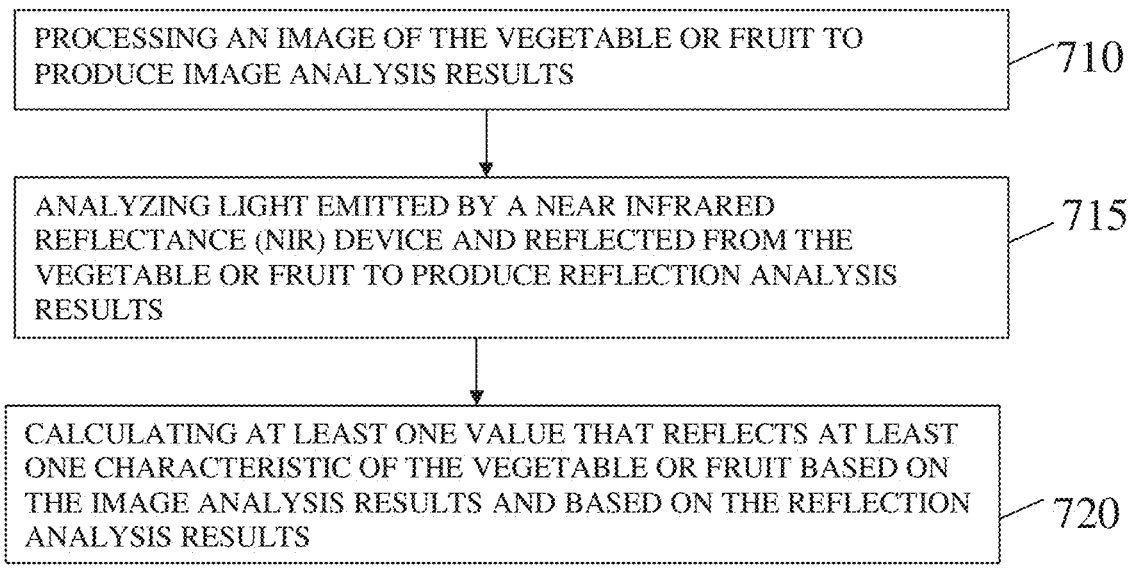
FIG. 7 shows a flowchart of a method according to illustrative embodiments of the present invention.

Reference is made to FIG. 7, which shows a flowchart of a method of none-destructively determining characteristics of a vegetable or fruit according to illustrative embodiments of the present invention. As shown by block 710, an image of a vegetable or fruit may be analyzed or otherwise processed to produce image analysis results. For example, an image of banana 3 captured by camera 166 may be analyzed by controller 105 or by server 150 to produce image analysis results 170 that include an indication, specification or any value or data that specifies the color of banana 3 and/or marks or patterns on the skin of banana 3 (e.g., size, amount or other attributes of spots, stripes and the like). Image analysis results 170 produced by controller 105 or by server 150 may include any data, information or value that can be derived or determined based on a digital image, for example, image analysis results 170 may include histograms or values representing imaging parameters or values such as color, brightness, saturation, transparency, contrast.

As shown by block 715, light emitted by a near infrared reflectance (NIR) device and reflected from the vegetable or fruit may be analyzed to produce reflection analysis results. For example, infrared light emitted by NIR device 165 may be captured, received or sensed by a sensor included in NIR device 165 or in computing device 100 may be analyzed by controller 105 or server 150 to produce reflection analysis results 171.

For example, light reflected from banana 3 may be captured and may be analyzed by controller 105 or server 150 to produce reflection analysis results 171 that include an indication, specification or any value or data that identifies or characterizes infrared light reflected from banana 3. For example, reflection analysis results 171 may include a spectrum, amplitudes, frequencies or any other information that identifies, specifies or characterizes an object based on light it reflects.

As shown by block 720, at least one value that reflects at least one characteristic of the vegetable or fruit may be calculated based on the image analysis results and based on the reflection analysis results.

For example, in some embodiments, controller 105 or server 150 uses image analysis results 170 and reflection analysis results 171 to calculate, for a specific fruit or vegetable, a first value that represents a ripeness and a second value that represents a quality. Controller 105 may then present the first and second values to a user. Various other values, attributes, characteristics or aspects of a fruit or vegetable may be calculated based on image analysis results 170 and reflection analysis results 171, for example, size, concertation or amount of water, fat, sugar or other substances, concentrations or measures of color, acidity, water, BRIX, size, acidity, pH level, firmness, texture and the like may all be calculated based on image analysis results 170 and reflection analysis results 171. Calculated and/or determined values, attributes, characteristics or aspects of a fruit or vegetable may be presented to a user. e.g., graphically as shown by FIG. 5. It is noted that a set of attributes, characteristics or aspects of a fruit or vegetable may be presented to a user on a single screen, e.g., the ripeness and quality of banana 3 may be graphically presented on a screen of a smartphone or laptop carried by a user. Accordingly, some embodiments provide a user with aggregated, valuable and relevant data that can be readily used by the user, e.g., based on indicated ripeness and quality, a user can decide which fruit on a shelf to buy.

In some embodiments, controller 105 or serer 150 obtains an indication or specification of the cultivar or genus (or of the specific species in a specific genus) of the vegetable or fruit and calculates the attributes or characteristics based on the cultivar. In some embodiments, using image processing, controller 105 identifies or determines the cultivar of a fruit, e.g., by comparing an image of the fruit to a set of images of known cultivars, in other embodiments the cultivar may be provided, e.g., by a user of computing device 100. Using a cultivar indication or specification can increase speed of operation and/or reduce false results. For example, lemon, lime and citron may look the same but a specific set of values of acidity, BRIX and acidity for a lemon indicates that the lemon is ripe yet the same specific set of values for a lime indicates or means that a lime is not yet ripe. Accordingly, controller 105 may first identify or determine the cultivar or genus and then calculates attributes for the fruit. If provided with a cultivar or genus, controller 105 can skip the cultivar determination process or step, thus speeding the process of none-destructively determining characteristics of a vegetable or fruit.

In some embodiments, characteristics as described may be calculated based on at least one of: a geographic region, a temperature and a date. For example, a specific set of values of pH level, sugar, BRIX and acidity of a lemon in Argentina may cause controller 105 to determine and inform the user that the lemon is ripe or is of high quality, while the same specific set of values of acidity, BRIX and acidity of a lemon in Africa may cause controller 105 to determine and inform the user that the lemon is not yet ripe or is of low quality. Similarly, the same specific set of values of a fruit obtained or calculated at two different dates (e.g., January and October) or two different temperatures or weather conditions may cause controller 105 to determine or calculate two different sets of characteristics or attributes, e.g., different ripeness or quality may be determined, based on same, similar or even identical values, for different countries or regions in a state, different time of year, different temperatures and/or any other parameter. For example, specific tables for values of a fruit with respect to specific geographic locations, dates, weather or ambient temperature may be stored in storage system 167, thus a first set of values (e.g., pH level, sugar, BRIX and acidity) can be mapped to a first set of characteristics (e.g., ripeness and quality) in a first country or date, and a second set of values can be mapped to a second set of characteristics (e.g., ripeness and quality) in a second country or date.

Controller 105 may calculate the at least one value for a plurality of vegetables or fruits. For example, an image acquired by camera 166 may be of several or even many grapes (e.g., in a cluster) in a box or on a shelf in a store, and controller 105 may calculate an average quality or an average ripeness for the cluster or box of grapes. For example, controller 105 may calculate a quality and/or ripeness for each of the grapes in an image of a cluster or box as described herein and may further calculate an average quality and/or ripeness for the cluster or box. Accordingly, an embodiment may provide a user with information such as ripeness or quality of a set or cluster for fruits or vegetables.

Controller 105 may determine and indicate or show, to a user, the best and worst fruit in a cluster or set. For example, having determined characteristics and attributes as described, for each of the fruits in an image, controller 105 may draw a circle around the best fruit, e.g., as shown by FIG. 6. Accordingly, an embodiment may enable a user to pick the best fruit from a set of fruits. For example, using scores and profiles as described herein, a user may provide controller 105 with a profile of a banana and controller 105 may indicate or show, in a set of bananas (a hand that consists of bananas, which are referred to as fingers) the banana that is closest to, or best matches the, profile. Accordingly, an embodiment enables a user to provide a profile of a fruit or vegetable and the embodiment may automatically find, in a set of fruits, the fruit that best matches the profile.

Controller 105 may use image analysis results 170, reflection analysis results 171, profiles 172, scores 173 and characteristics 174 to calculate and provide a prediction related to at least one of: harvesting and treating of crops. Other data such as publications of various farmers or industry organizations may be used by controller 105 to calculate and provide a prediction. For example, a prediction may be calculated, or an action may be suggested by controller 105 based on image analysis results 170, reflection analysis results, 171 characteristics 174, e.g., for a specific cultivar or genus, and further based on weather conditions or forecast (e.g., rain expected in 7 days, low temperatures etc.). For example, controller 105 may suggest a date for harvesting based on: how ripe oranges in a citrus grove are, the quality of the oranges, a weather forecast, a demand in the market and so on and/or, controller 105 may predict that oranges in the grove will be ready for picking in 5 days.

The term "characteristics" of a subject as referred to herein may mean or refer to any or all of attributes, classifications, description and/or other aspects related to a substance such as a fruit or vegetable as further described herein. Characteristics 174 may include any characteristics of a fruit or vegetable.

In some embodiments, characteristics 174 include any characteristics of a subject, e.g., characteristics calculated based on image analysis results 170 and reflection analysis results 171 as described. Profiles 172 may include data similar to the data in characteristics 174, that is, a profile 172 may include a specific set of characteristics that describes or identifies a specific condition of a fruit or vegetable, e.g., a profile includes a ripeness level, a quality indication, a sugar level, a pH level and so on, and thus the profile describes a fruit or vegetable in a specific condition. A characteristic 174 of a fruit or vegetable may be compared or matched with a profile 172. For example, controller 105 uses image analysis results 170 and reflection analysis results 171 and other data as described to calculate characteristics 174 for a banana and then compares data in the characteristics 174 profiles 172 in order to find a match, a profile 172 with characteristics that are same or similar to those in characteristics 174. Matching characteristics 174 of a fruit or vegetable with a profile 172 may be, or may include classifying the fruit or vegetable, e.g., a profile may include, or be associated with, a classification.

In some embodiments, a profile 172 is associated with a score 173 and a scoring, classification or description of a fruit or vegetable may be based on the profile and associated score. For example, if characteristics 174 of a fruit is matched with a profile 172 then the score that is associated with profile 172 may be given, or associated with the fruit. As described, characteristics 174 matches a profile 172 if at least some of the attributes, values, parameters or descriptions of in characteristics 174 are same, similar or close to those in profile 172, e.g., one or more of a color, acidity, BRIX, size, sugar concentration. Ph level, firmness in the characteristics 174 and profile 172 are the same or with a difference that is below a threshold.

In some embodiments, a score associated with a profile may be set or provided by a user of computing device or it may be received from server 150. In some embodiments, a profile and a score may be based on input from a plurality of sources. For example, server 150 may receive scores given or assigned to, or associated with, a profile, and server 150 may use the scores to calculate a global standard or score for the profile. Server 150 may receive profiles from a plurality of users, e.g., a user may select a banana for which a characteristics 174 object was generated and stored as described, and, if the user likes the banana he/she chose to buy, the user can cause controller 105 to generate a profile 172 based on the characteristics 174 of the banana and may then upload or share the profile thus enabling other users to select a banana that is substantially identical or similar to the one chosen by the user. Profiles and scores may be created, updated, communicated and shared between any group of uses, e.g., a community in a social network.

A specific profile and/or score may be designated as a reference such that a standard is provided. For example, retailers, users or organizations can easily and readily define a reference or standard profile and/or an associated score, thus enabling a crowd of users, an organization or even a group of organizations to unambiguously and coherently communicate with respect to fruits or vegetables. For example, retailers can set prices based on profiles, cooking recipes may include profiles etc. A standard (e.g., in the form of a profile and/or score) may be related to any aspect, e.g., a standard may include a level or value of ripeness or quality as described. Controller 105 may provide a user with information based on a standard profile. Controller 105 may calculate, for a fruit or vegetable, at least one value based on comparing a reference profile to at least one of: image analysis results 170 and reflection analysis results 171 produced for the fruit or vegetable as described.

For example, controller 105 may show the user how similar/different a specific fruit in a store is to/from a standard profile, controller 105 may indicate which specific values or characteristics of a fruit are similar, same or close to those in a profile, which specific values or characteristics of a fruit are different from those in a profile and so on.

In some embodiments, controller 105 may cause a machine to select a fruit or vegetable based on at least one of: a profile and a score. For example, profiles 172 and scores 173 may be provided to a controller 105 in a packaging facility and based on a match of fruits with a profile controller 105 may cause actuators, openings or other devices to select or route fruits. For example, controller 105 may cause a machine to route fruits that match a premium quality profile to a first destination or box, route fruits that match a high-quality profile to a second destination or box and route fruits that match a low-quality profile to a third destination or box.

In the description of the present application, each of the verbs, "comprise" "include" and "have", and conjugates thereof, are used to indicate that the object or objects of the verb are not necessarily a complete listing of components, elements or parts of the subject or subjects of the verb. Unless otherwise stated, adjectives such as "substantially" and "about" modifying a condition or relationship characteristic of a feature or features of an embodiment of the disclosure, are understood to mean that the condition or characteristic is defined to within tolerances that are acceptable for operation of an embodiment as described. In addition, the word "or" is considered to be the inclusive "or" rather than the exclusive or, and indicates at least one of, or any combination of items it conjoins.

Descriptions of embodiments of the invention in the present application are provided by way of example and are not intended to limit the scope of the invention. The described embodiments comprise different features, not all of which are required in all embodiments. Some embodiments utilize only some of the features or possible combinations of the features. Variations of embodiments of the invention that are described, and embodiments comprising different combinations of features noted in the described embodiments, will occur to a person having ordinary skill in the art. Unless explicitly stated, the method embodiments described herein are not constrained to a particular order in time or chronological sequence. Additionally, some of the described method elements may be skipped, or they may be repeated, during a sequence of operations of a method.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

Various embodiments have been presented. Each of these embodiments may of course include features from other embodiments presented, and embodiments not specifically described may include various features described herein.

The invention claimed is:

1. A method of non-destructively determining characteristics of a vegetable or fruit, the method comprising:
creating at least one profile for a cultivar of a vegetable or fruit;
processing an image of a vegetable or fruit to produce image analysis results;
analyzing light emitted by a Near Infrared Reflectance (NIR) device and reflected from the vegetable or fruit to produce reflection analysis results; and
calculating, and presenting to a user, a score for the vegetable or fruit based on matching the image and reflection analyses results with the profile.

2. The method of claim 1, wherein the profile and the analyses results include a value that represents a ripeness and a value that represents a quality.

3. The method of claim 1, further comprising:
obtaining a cultivar of the vegetable or fruit; and
calculating the at least one value based on the cultivar.

4. The method of claim 1, further comprising calculating the at least one value based on at least one of: a geographic region and a date.

5. The method of claim 1, further comprising:
receiving an image of a plurality of vegetables or fruit; and
calculating, for the plurality of vegetables or fruit, scores of the best and worst vegetable or fruit.

6. The method of claim 1, further comprising calculating a prediction related to at least one of: harvesting and treating of crops.

7. The method of claim 1, further comprising:
receiving, from a plurality of users, profiles and associated scores; and
creating the profile and associating the profile with a score based on the profiles and associated scores received from the users.

8. The method of claim 7, further comprising using input from a plurality of users for at least one of: creating the profile and calculating the score.

9. The method of claim 7, further comprising:
designating at least one of: a profile and a score, as a reference; and
calculating the at least one value based on comparing at least one reference to at least one of: the image analysis results and the reflection analysis results.

10. The method of claim 7, further comprising: causing a machine to select a fruit or vegetable based on at least one of: a profile and a score.

11. A system comprising:
a memory; and
a controller configured to:
create at least one profile for a cultivar of a vegetable or fruit;
process an image of the vegetable or fruit to produce image analysis results;
analyze light emitted by a Near Infrared Reflectance (NIR) device and reflected from the vegetable or fruit to produce reflection analysis results; and
calculate, and present to a user, a score for the vegetable or fruit based on matching the image and reflection analyses results with the profile.

12. The system of claim 11, wherein the profile and the analyses results include a first value that represents a ripeness and a second value that represents a quality.

13. The system of claim 11, wherein the controller is further configured to:
obtain a cultivar of the vegetable or fruit; and
calculate the at least one value based on the cultivar.

14. The system of claim 11, wherein the controller is further configured to calculate the at least one value based on at least one of: a geographic region and a date.

15. The system of claim 11, wherein the controller is further configured to:
receive an image of a plurality of vegetables or fruit;
calculate, for the plurality of vegetables or fruit, scores of the best and worst vegetables or fruits.

16. The system of claim 11, wherein the controller is further configured to calculate a prediction related to at least one of: harvesting and treating of crops.

17. The system of claim 11, wherein the controller is further configured to:
receive, from a plurality of users, profiles and associated scores; and
create the profile and associate the profile with a score based on the profiles and associated scores received from the users.

18. The system of claim 17, wherein the controller is further configured to use input from a plurality of users for at least one of: creating the profile and calculating the score.

19. The system of claim 17, wherein the controller is further configured to:
designate at least one of: a profile and a score, as a reference; and
calculate the at least one value based on comparing at least one reference to at least one of:
the image analysis results and the reflection analysis results.

20. The system of claim 17, wherein the controller is further configured to cause a machine to select a fruit or vegetable based on at least one of: a profile and a score.

* * * * *